United States Patent [19]

Inoue et al.

[11] Patent Number: 4,781,857

[45] Date of Patent: * Nov. 1, 1988

[54] HALOGEN-CONTAINING PYRIDINE COMPOUND AND LIQUID CRYSTAL COMPOSITION

[75] Inventors: Hiromichi Inoue; Takashi Inukai; Kouji Ohno; Shinichi Saito; Kazutoshi Miyazawa, all of Kanagawa, Japan

[73] Assignee: Chisso Corporation, Ohsaka, Japan

[*] Notice: The portion of the term of this patent subsequent to Aug. 23, 2005 has been disclaimed.

[21] Appl. No.: 28,691

[22] Filed: Mar. 20, 1987

[30] Foreign Application Priority Data

Mar. 26, 1986 [JP] Japan ................... 61-67960

[51] Int. Cl.$^4$ .............. G02F 1/13; C09K 19/34; C07D 211/7; C07D 211/82
[52] U.S. Cl. .................. 252/299.61; 252/229.01; 252/299.5; 350/350 R; 350/350.5; 546/339
[58] Field of Search .......... 252/299.01, 299.5, 299.61; 250/350 R, 350 S; 546/339

[56] References Cited

U.S. PATENT DOCUMENTS

| | | | |
|---|---|---|---|
| 4,622,165 | 11/1986 | Kano et al. | 252/299.01 |
| 4,684,220 | 8/1987 | Shionozaki et al. | 252/299.61 |
| 4,684,477 | 8/1987 | Sugimori et al. | 252/299.61 |

FOREIGN PATENT DOCUMENTS

| | | | |
|---|---|---|---|
| 194153 | 9/1986 | European Pat. Off. | 252/299.61 |
| 206228 | 12/1986 | European Pat. Off. | 252/299.61 |
| 3315295 | 10/1984 | Fed. Rep. of Germany | 252/299.61 |
| 3515373 | 11/1986 | Fed. Rep. of Germany | 252/299.61 |
| 61-91284 | 5/1986 | Japan | 252/299.61 |
| 8606401 | 11/1986 | PCT Int'l Appl. | 252/299.61 |
| 2092169 | 8/1982 | United Kingdom | 252/299.61 |
| 2161808 | 1/1986 | United Kingdom | 252/299.61 |

OTHER PUBLICATIONS

Pavluchemko, A. I., et al., Advances in Liquid Crystal Research and Applications, Data, L., Pergamon Press, Oxford, pp. 1007–1013, (1980).

Demus, D., et al., Flüssige Kristalle in Tabellen II, VEB Deutscher Verlag fur Grumdstoffihaustrie, Leipzig, pp. 363–364, (1984).

Gray, G. W., et al., Liquid Crystals & Plastic Crystals, vol. 1, pp. 165–166, John Wiley & Sons, N.Y., (1974).

Primary Examiner—Teddy S. Gron
Attorney, Agent, or Firm—Wenderoth, Lind & Ponack

[57] ABSTRACT

A novel liquid crystal compound exhibiting SC phase which, when added to an optically active liquid crystal, makes the resulting chiral smectic liquid crystal material exhibit superior performances in liquid crystal display elements utilizing the ferroelectricity of the material, and a chiral smectic C composition using the compound. The compound is expressed by the formula

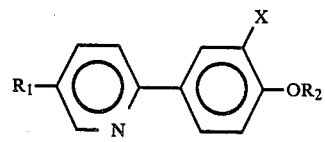

wherein X represents F or Cl and $R_1$ and $R_2$ each represent a straight chain alkyl group of 1 to 18 carbon atoms.

5 Claims, No Drawings

HALOGEN-CONTAINING PYRIDINE COMPOUND AND LIQUID CRYSTAL COMPOSITION

BACKGROUND OF THE INVENTION

1. Field of the Invention

This invention relates to a novel compound and a chiral smectic C (SC*) liquid crystal composition containing the compound and being useful for liquid crystal display elements.

2. Description of the Related Art

At present, as to liquid crystal display elements, TN (Twisted Nematic) type display mode has been most broadly employed, but as far as the response speed is concerned, such TN type display elements are inferior to emissive type display elements (such as those of electroluminescence, plasma display, etc.). Although various improvements in this respect have been attempted, it appears that improvement to a large extent has not yet been realized. Thus, various liquid crystal display devices based on a different principle from that of TN type display elements have been attempted. As one of such devices, there is a display mode utilizing a ferroelectric liquid crystal (N. A. Clark et al: Applied Phys. lett., 36, 899 (1980)). This mode utilizes the chiral smectic C phase (hereinafter abbreviated to SC* phase) or the chiral smectic H phase (hereinafter abbreviated to SH* phase) of the ferroelectric liquid crystal, and those having these phases in the vicinity of room temperature are preferred.

These chiral smectic liquid crystal materials may be obtained by blending a plurality of single compounds each exhibiting a chiral smectic phase by itself, but it is known that the materials may be also obtained by adding an optically active liquid crystal compound, preferably a chiral smectic liquid crystal compound to an achiral smectic liquid crystal (exhibiting smectic C phase (SC phase), smectic H phase (SH phase), etc.).

Various kinds of compounds exhibiting SC phase have been known, but as to whether or not chiral smectic liquid crystal materials obtained by adding an optically active liquid crystal to the above-mentioned known compounds exhibit superior performances in liquid crystal display utilizing ferroelectricity, no ultimate evaluation thereof has been yet obtained. This is due to the fact that liquid crystal display utilizing ferroelectricity has not yet been technically completed. Thus it is necessary in the present situation to test various novel SC materials.

SUMMARY OF THE INVENTION

The main object of the present invention is to provide a novel liquid crystal compound exhibiting SC phase which is suitable for the above-mentioned use.

The present invention resides in a halogen-containing pyridine compound, i.e. a 2-(m-halogeno-p-alkoxyphenyl)-5-alkylpyridine, expressed by the formula

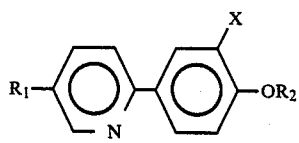

(I)

wherein X represents F or Cl and $R_1$ and $R_2$ each represents an alkyl group of 1 to 18 carbon atoms, and a chiral smectic liquid crystal composition comprising at least one of said liquid crystal compounds and at least one optically active liquid crystal compound.

The present applicants have previously filed U.S. application Ser. No. 003,282 entitled "Halogen-containing heterocyclic compound", filed on Jan. 14, 1987. This application is directed to a compound expressed by the formula

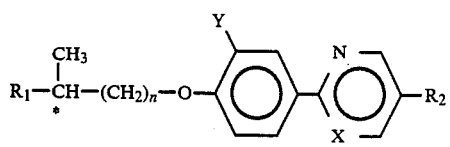

wherein $R_1$ and $R_2$ each represents a $C_2$-$C_{18}$ alkyl group; X represents —N= or —CH=; Y represents F or Cl; n represents 0 or an integer of 1 to 10; and the symbol * represents an asymmetric carbon atom.

The case where X represents —CH= in the above formula corresponds to the case where $R_2$ of the present invention is changed to an optically active group. Thus, the compounds of the prior invention naturally exhibit SC* phase, whereas the compounds of the present invention exhibit no SC* phase. Further, in the compounds of the present invention, those exhibiting SC phase have a tendency that their upper limit temperatures are higher than those of SC* phase of the corresponding optically active substances.

DETAILED DESCRIPTION OF PREFERRED EMBODIMENTS

Concrete examples of representative compounds of the formula (I) are as follows:

2-(m-fluoro-p-ethoxyphenyl)-5-ethylpyridine, 2-(m-fluoro-p-butoxyphenyl)-5-ethylpyridine, 2-(m-fluoro-p-hexyloxyphenyl)-ethylpyridine, 2-(m-fluoro-p-octyloxyphenyl)-ethylpyridine, 2-(m-fluoro-p-octadecyloxyphenyl)-5-ethylpyridine, 2-(m-fluoro-p-methoxyphenyl)-5-propylpyridine, 2-(m-fluoro-p-butoxyphenyl)-5-propylpyridine, 2-(m-fluoro-p-nonyloxyphenyl)-5-propylpyridine, 2-(m-fluoro-p-dodecyloxyphenyl)-5-propylpyridine, 2-(m-fluoro-p-pentoxyphenyl)-5-butylpyridine, 2-(m-fluoro-p-octyloxyphenyl)-5-butylpyridine, 2-(m-fluoro-p-decyloxyphenyl)-5-butylpyridine, 2-(m-fluoro-p-ethoxyphenyl)-5-pentylpyridine, 2-(m-chloro-p-pentyloxyphenyl)-5-pentylpyridine, 2-(m-fluoro-p-octyloxyphenyl)-5-pentylpyridine, 2-(m-chloro-p-nonyloxyphenyl)-5-pentylpyridine, 2-(m-flouro-p-dodecyloxyphenyl)-5-pentylpyridine, 2-(m-fluoro-p-methoxyphenyl)-5-hexylpyridine, 2-(m-chloro-p-ethoxyphenyl)-5-hexylpyridine, 2-(m-fluoro-p-propoxyphenyl)-5-hexylpyridine, 2-(m-chloro-p-butoxyphenyl)-hexylpyridine, 2-(m-fluoro-p-heptyloxyphenyl)-5-hexylpyridine, 2-(m-chloro-p-octyloxyphenyl)-5-hexylpyridine, 2-(m-fluoro-p-decyloxyphenyl)-5-hexylpyridine, 2-(m-fluoro-p-tetradecyloxyphenyl)-5-hexylpyridine, 2-(m-chloro-p-propoxyphenyl)-2-heptylpyridine, 2-(m-fluoro-p-pentoxyphenyl)-5-heptylpyridine, 2-(m-fluoro-p-hexyloxyphenyl)-5-heptylpyridine, 2-(m-chloro-p-heptyloxyphenyl)-5-heptylpyridine, 2-(m-fluoro-p-octyloxyphenyl)-5-heptylpyridine, 2-(m-fluoro-p-nonyloxyphenyl)-5-heptylpyridine, 2-(m-fluoro-p-decyloxyphenyl)-5-heptylpyridine, 2-(m-fluoro-p-dodecyloxyphenyl)-5-heptylpyridine, 2-(m-fluoro-p-tetradecyloxyphenyl)-5-heptylpyridine, 2-(m-chloro-p-decyloxyphenyl)-5-heptylpyridine, 2-(m-fluoro-p-methoxyphenyl)-octylpyridine, 2-(m-fluoro-p-propoxyphenyl)-5-octylpyridine, 2-(m-fluoro-p-butoxyphenyl)-5-octylpyridine, 2-(m-chloro-p-heptyloxyphenyl)-5-octylpyridine, 2-(m-fluoro-p-octyloxyphenyl)-5-octylpyridine, 2-(m-fluoro-p-nonyloxyphenyl)-5-octylpyridine, 2-(m-fluoro-p-decyloxyphenyl)-5-octylpyridine, 2-(m-fluoro-p-undecyloxyphenyl)-5-octylpyridine, 2-(m-fluoro-p-tetradecyloxyphenyl)-5-octylpyridine, 2-(m-fluoro-p-octadecyloxyphenyl)-5-octylpyridine, 2-(m-chloro-p-methoxyphenyl)-5-nonylpyridine, 2-(m-fluoro-p-propoxyphenyl)-5-nonylpyridine, 2-(m-chloro-p-butoxyphenyl)-5-nonylpyridine, 2-(m-fluoro-p-hexyloxyphenyl)-5-nonylpyridine, 2-(m-chloro-p-hexyloxyphenyl)-5-nonylpyridine, 2-(m-fluoro-p-heptyloxyphenyl)-5-nonylpyridine, 2-(m-fluoro-p-decyloxyphenyl)-5-nonylpyridine, 2-(m-fluoro-p-dodecyloxyphenyl)-5-nonylpyridine, 2-(m-chloro-p-tridecyloxyphenyl)-5-nonylpyridine, 2-(m-fluoro-p-hexadecyloxyphenyl)-5-nonylpyridine, 2-(m-fluoro-p-methoxyphenyl)-5-nonylpyridine, 2-(m-fluoro-p-methoxyphenyl)-5-decylpyridine, 2-(m-fluoro-p-butoxyphenyl)-5-decylpyridine, 2-(m-fluoro-p-pentoxyphenyl)-decylpyridine, 2-(m-chloro-p-pentoxyphenyl)-5-decylpyridine, 2-(m-fluoro-p-heptyloxyphenyl)-2-decylpyridine, 2-(m-fluoro-p-nonyloxyphenyl)-5-decylpyridine, 2-(m-fluoro-p-dodecyloxyphenyl)-dodecylpyridine, 2-(m-fluoro-p-ethoxyphenyl)-dodecylpyridine, 2-(m-fluoro-p-propoxyphenyl)dodecylpyridine, 2-(m-fluoro-p-butoxyphenyl)dodecylpyridine, 2-(m-fluoro-p-pentoxyphenyl)dodecylpyridine, 2-(m-chloro-p-hexyloxyphenyl)-5-dodecylpyridine, 2-(m-fluoro-p-heptyloxyphenyl)-dodecylpyridine, 2-(m-fluoro-p-decyloxyphenyl)-5-dodecylpyridine, 2-(m-fluoro-p-ethoxyphenyl)-5-tetradecylpyridine, 2-(m-fluoro-p-butoxyphenyl)-5-tetradecylpyridine.

The phase transition points of a part of the above compounds are shown in Table 1.

TABLE 1

| Sample No. | In formula (I) R$^1$ | X | R$^2$ | Phase transition points (°C.) C | S$_C$ | S$_A$ | N | I |
|---|---|---|---|---|---|---|---|---|
| 1 | C$_6$H$_{13}$ | F | CH$_3$ | . 52.6 | — | — | — | . |
| 2 | C$_6$H$_{13}$ | F | C$_7$H$_{15}$ | . 33.0 | . 34.0 | . 35.0 | . 39.7 | . |
| 3 | C$_6$H$_{13}$ | F | C$_{10}$H$_{21}$ | . 42.8 | (. 37.9) | — | . 45.8 | . |
| 4 | C$_7$H$_{15}$ | F | CH$_3$ | . 49.1 | — | — | — | . |
| 5 | C$_7$H$_{15}$ | F | C$_6$H$_{13}$ | . 25.0 | . 40.6 | . 50.5 | — | . |
| 6 | C$_7$H$_{15}$ | F | C$_7$H$_{15}$ | . 32.5 | . 40.1 | . 50.4 | — | . |
| 7 | C$_7$H$_{15}$ | F | C$_8$H$_{17}$ | . 26.0 | . 46.0 | . 53.4 | — | . |
| 8 | C$_7$H$_{15}$ | F | C$_9$H$_{19}$ | . 37.0 | . 45.0 | . 53.6 | — | . |
| 9 | C$_8$H$_{17}$ | F | CH$_3$ | . 46.3 | — | — | — | . |
| 10 | C$_8$H$_{17}$ | F | C$_8$H$_{17}$ | . 34.7 | . 49.9 | . 54.8 | — | . |
| 11 | C$_8$H$_{17}$ | F | C$_9$H$_{19}$ | . 47.0 | . 50.3 | . 55.4 | — | . |
| 12 | C$_8$H$_{17}$ | F | C$_{10}$H$_{21}$ | . 44.0 | . 53.2 | . 56.5 | — | . |
| 13 | C$_8$H$_{17}$ | F | C$_{11}$H$_{23}$ | . 54.3 | (. 52.4) | . 56.5 | — | . |
| 14 | C$_9$H$_{19}$ | F | CH$_3$ | . 47.5 | — | — | — | . |
| 15 | C$_9$H$_{19}$ | F | C$_7$H$_{15}$ | . 35.0 | . 45.6 | . 57.6 | — | . |
| 16 | C$_9$H$_{19}$ | F | C$_{12}$H$_{25}$ | . 46.3 | . 57.8 | . 62.1 | — | . |
| 17 | C$_{10}$H$_{21}$ | F | CH$_3$ | . 53.5 | — | — | — | . |
| 18 | C$_{10}$H$_{21}$ | F | C$_5$H$_{11}$ | . 38.4 | (. 23.4) | . 55.0 | — | . |
| 19 | C$_{10}$H$_{21}$ | F | C$_9$H$_{19}$ | . 46.7 | . 57.8 | . 61.4 | — | . |

A greater part of the compounds of the formula (I) are liquid crystal substances solely exhibiting, smectic, C phase (SC phase), and by blending them with other optically active compounds, preferably optically active liquid crystal compounds, more preferably chiral smectic C liquid crystal compounds, it is possible to obtain liquid crystal materials exhibiting chiral smectic C phase (SC* phase) within a broad temperature range. As to the compounds of the formula (I), although those which by themselves exhibit SC phase are preferred, even those which are not observed to solely exhibit SC phase may also be used. Preferable compounds among those of the formula (I) are those number wherein the total of the carbon atoms of R$_1$ and R$_2$ is in the range of 4 to 24. Further, more preferable compounds of the formula (I) are those with R$_1$ of 6 to 12 carbon atoms, R$_2$ of 4–12 carbon atoms and X=F. Since these compounds exhibit SC phase within a broad temperature range including temperatures in the vicinity of room temperature, as illustrated in Table 1, they are very suitable substances for constituting ferroelectric liquid crystal compositions.

Further, the liquid crystal compounds of the formula (I) have superior compatibility with other optically active compounds, particularly chiral smectic liquid crystal compounds having SC* phase and SH* phase, compounds exhibiting cholesteric phase, etc.; hence when the compounds of the formula (I) are blended with the latter compounds, they exhibit a superior effect of broadening the temperature range of SC* phase exhibited by chiral smectic liquid crystal compositions, particularly the low temperature range thereof.

A specific feature of the compound of the present invention consists in that the halogen atom is laterally present as a substituent from the aspect of chemical structure. At present it is difficult to anticipate what change will occur in the phase transition points in a specified liquid crystal compound when the hydrogen atom at an unsubstituted position is replaced by a halogen atom (or another substituent). It may be generally said that the upper limit temperature in a liquid crystalline state (clearing point) will lower, but its extent cannot be presumed so that there is no method other than that of preparing a specified substance and actually observing its temperature. This applies also to even a relatively simple case as in nematic state, and it applies much more to the smectic state which is an object of the present invention, where the phase transition points of various smectic modification are present. In the compound of the present invention, it has been found that this lateral halogen atom substituent affords an extremely preferred effect.

The effect of introducing such a halogen atom will be concretely described by way of the following example:

Substituent (A): 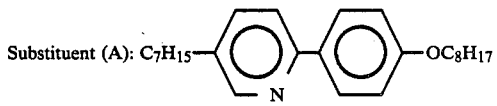

Phase transition points:

C $\xrightarrow{45.0°\,C.}$ SG $\xrightarrow{45.5°\,C.}$ SF $\xrightarrow{56.5°\,C.}$ SC $\xrightarrow{80.4°\,C.}$ I Halogen substituent (B): 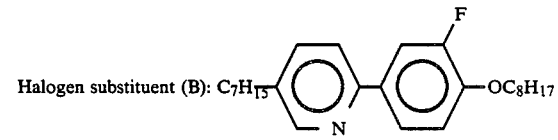

(a compound of the formula (I) wherein R$_1$ = C$_7$H$_{15}$, X = F and R$_2$ = C$_8$H$_{17}$)

Phase transition points:

C $\xrightarrow{26.0°\,C.}$ SC $\xrightarrow{46.0°\,C.}$ SA $\xrightarrow{53.4°\,C.}$ I As apparent from the above comparison, the effect of the halogen introduction in the formula (I) of the present invention consists in that appearance of other undesirable smectic phases at lower temperatures than that of SC phase is greatly inhibited. Namely, in the case of compound (A), SF and SG phases appear below SC phase, whereas in the case of compound (B), such phases are not observed at all. Further, as optically active compounds to be blended with the compounds of the present invention, those exhibiting chiral smectic C phase are preferred, but even in the case of compounds exhibiting no chiral smectic C phase, a liquid crystal composition exhibiting chiral smectic C phase may often be obtained by blending such compounds with those of the present invention.

Next, preparation of the compounds of the present invention will be described. The compounds of the formula (I) may be prepared through the following route:

keeping the mixture with stirring at room temperature for 8 hours, then adding water (500 ml), transferring the mixture into a separating funnel (this being a solution of a compound of the formula (IV) wherein X=F). To this aqueous solution were added a solution of conc. sulfuric acid (25 ml) and water (500 ml), followed by dissolving the deposited crystals in fresh toluene, drying this toluene solution of a compound of the formula (V) wherein X=F with calcium chloride, further dropwise and slowly adding thionyl chloride (150 ml) under cooling, keeping reflux on heating for one hour, thereafter distilling off the solvent and excess thionyl chloride under reduced pressure and recrystallizing the residue from heptane to obtain m-fluoro-p-methoxyphenyl β-chlorovinyl ketone (a compound of the formula (VI) wherein X=F) (83 g).

(ii) N-nonenylpiperidine (a compound of the formula (VII) wherein $R_1=C_7H_{15}$; b.p. 103° C./3.5 mmHg) (39 g, 0.176 mol) and triethylamine (17.8 g, 0.176 mol) were

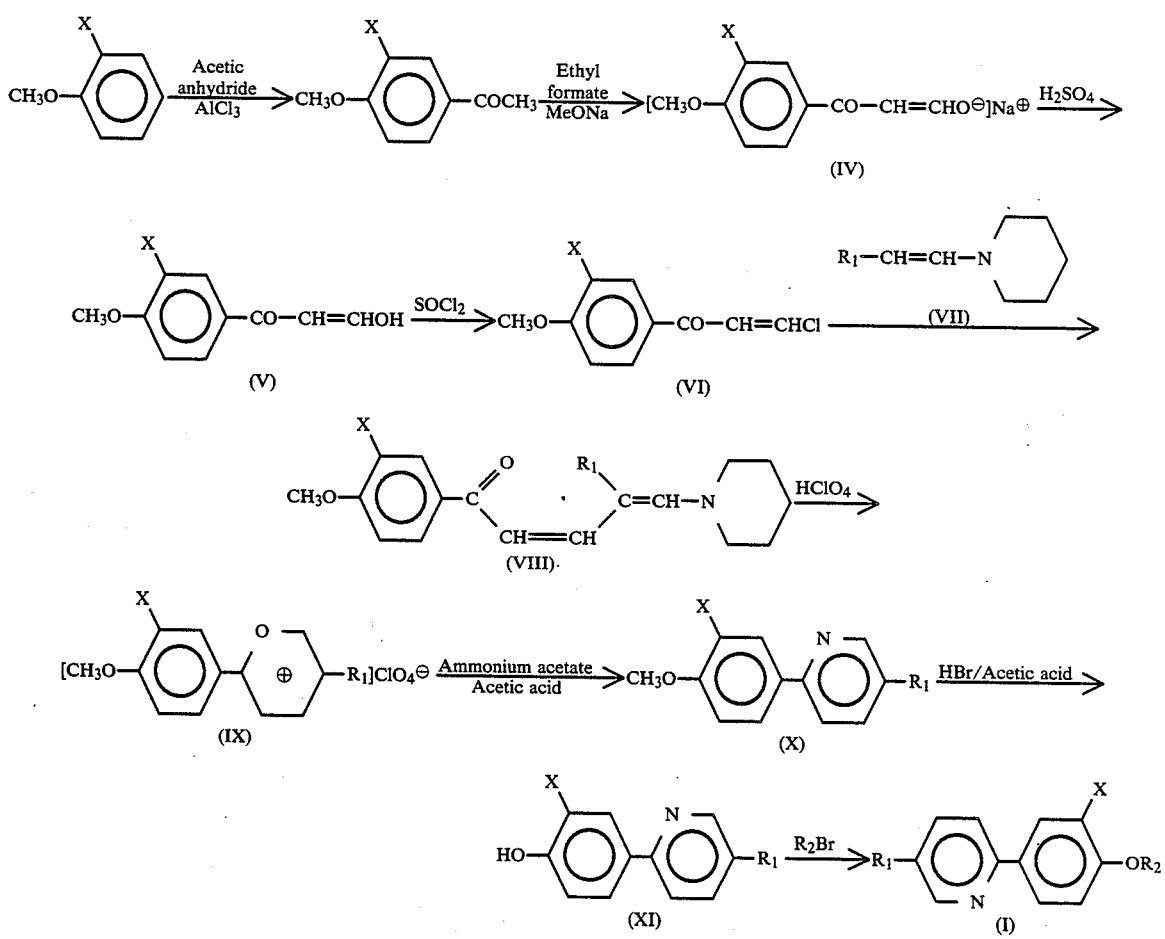

The compound and the liquid crystal composition will now be described by way of Examples.

EXAMPLE 1

Preparation of 2-(m-fluoro-p-hexyloxyphenyl)-5-heptyl-pyridine (a compound of the formula (I) wherein $R_1=C_7H_{15}$, X=F and $R_2=C_6H_{13}$; sample No. 5)

(i) To sodium methoxide (37.2 g, 0.688 mol) and toluene (2.1 l) agitated at room temperature were dropwise added a solution of m-fluoro-p-methoxyacetophenone (150.1 g, 0.625 mol) as a known substance, ethyl formate (46.3 g, 0.625 mol) and toluene (700 ml), followed by dissolved in ethyl ether (160 ml) with stirring, followed by dropwise adding to the resulting solution, a solution of m-fluoro-p-methoxyphenyl β-chlorovinyl ketone (VI) (35 g, 0.176 mol) obtained above, dissolved in ethyl ether (400 ml), while the temperature of the system was kept at 35° C. or lower, agitating the mixture at room temperature for 8 hours, adding water (100 ml) and toluene (100 ml), transferring the mixture into a separating funnel, twice washing the resulting organic layer with water, distilling off the solvent from the organic layer under reduced pressure, slowly adding perchloric acid (70%) (80 ml) to the residue (a compound of the formula (VIII) wherein $R_2 = C_7H_{15}$ and $X = F$) adding water (80 ml), refluxing the mixture on heating for 10 minutes, cooling, washing the resulting crystals with ethyl ether and drying them to obtain 2-(m-fluoro-p-methoxyphenyl)-5-heptylpyrilium perchlorate (a compound of the formula (IX) wherein $R_1 = C_7H_{15}$ and $X = F$) (23 g). N-nonenylpiperidine as the raw material was prepared from n-nonylaldehyde and piperidine according to Mannich et al's method (Chem. Ber., 69, 2106 (1936)).

(iii) 2-(m-Fluoro-p-methoxyphenyl)-5-heptylpyrilium perchlorate (123.0 g, 0.057 mol), ammonium acetate (44.1 g, 0.570 mol) and acetic acid (500 ml) were heated under reflux with stirring for 4 hours, followed by pouring the reaction fluid in water, dissolving the resulting crystals in toluene, transferring the solution into a separating funnel, three times washing it with water, distilling off the solvent under reduced pressure and recrystallizing the residue to obtain 2-(m-fluoro-p-methoxyphenyl)-5-heptylpyridine (a compound of the formula (X) wherein $R_1 = C_7H_{15}$, $R_2 = CH_3$ and $X = F$) (13 g) having a m.p. of 49.1.

(iv) 2-(m-Fluoro-p-methoxyphenyl)-5-heptylpyridine (X) (13 g, 0.043 mol) obtained at the step (III) hydrobromic acid (47%) (50 ml) and acetic acid (140 ml) were heated under reflux for 30 hours, followed by cooling the reaction fluid, pouring it in water, filtering off the resulting crystals, dissolving the crystals in 2N-NaOH aqueous solution (about 100 ml), further adding acetic acid (30 ml) to obtain an acidic solution filtering off deposited crystals and recrystallizing them from ethyl alcohol to obtain 2-(m-fluoro-p-hydroxyphenyl)-5-heptylpyridine (a compound of the formula (XI) wherein $X = f$ and $R_1 = C_7H_{15}$) (7.2 g) having a m.p. of 83.7°–86.1° C.

In addition, compounds of the formula (XI) wherein $X = F$ and $R = C_6H_{13}$, $X = F$ and $C_8H_{17}$, and $X = F$ and $C_{10}H_{21}$ had melting points of 100.7°–103.0° C., 73.5°–74.6° C. and 46.8°–48.3° C., respectively.

(v) 2-(m-Fluoro-p-hydroxyphenyl)-5-heptylpyridine (2 g, 0.007 mol), ethanol (20 ml), potassium hydroxide (0.48 g, 0.008 mol) and n-hexylbromide (1.4 g, 0.008 mol) were heated under reflux with stirring for 4 hours, followed by cooling the resulting reaction fluid, adding water and toluene, transferring the mixture into a separating funnel, washing the resulting organic layer with 2N-NaOH aqueous solution, then washing it with water, distilling off the solvent under reduced pressure, recrystallizing the residue from ethanol, filtering off it in a refrigerator and drying it to obtain the objective final product 2-(m-fluoro-p-hexyloxyphenyl)-5-heptylpyridine (1.7 g).

This product had a C-SC point of 25.0° C., a SC-SA point of 40.6° C. and a SA-I point of 50.5° C. Further its elemental analysis values accorded well with its calculated values as follows:

|   | Observed values (%) | Calculated values (%) (in terms of $C_{24}H_{34}FNO$) |
|---|---|---|
| C | 77.5 | 77.59 |
| H | 9.0 | 9.22 |
| F | 5.0 | 5.11 |
| N | 3.6 | 3.77 |

Example 1 was repeated except that 2-(m-fluoro-p-methoxyphenyl)-5-heptylpyrilium perchlorate at the step (iii) was replaced by other 2-(m-fluoro-p-methoxyphenyl)-5-alkylpyrilium perchlorates and hexylbromide at the step (v) was replaced by various alkylbromides, to obtain any of the other compounds of the formula (I).

EXAMPLE 2 (COMPOSITION EXAMPLE 1)

Eight kinds of compounds of the present invention (sample Nos. 2, 3, 5, 7, 10, 13, 18 and 19) were blended together each in equal weights to prepare a liquid crystal composition A, which had a m.p. of −19° C., exhibited SC phase at temperatures higher than the above one, formed SA phase at 38° C. and formed an isotropic liquid at 51° C.

To 60 parts by weight of this liquid crystal composition A were added the following two kinds of chiral smectic liquid crystal compounds C and D each in 20 parts by weight and they were blended to prepare a chiral smectic liquid crystal composition B.

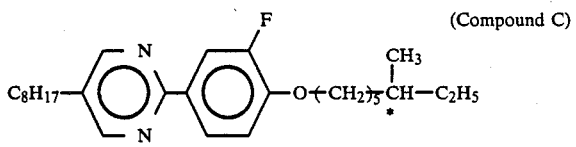
(Compound C)

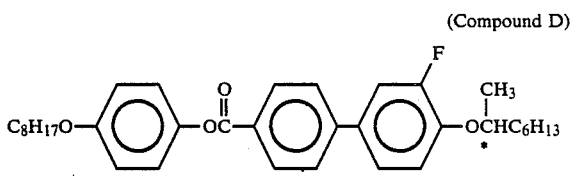
(Compound D)

The SC* phase of the thus obtained chiral smectic liquid crystal composition B had an upper limit temperature of 37° C. and no crystallization was observed down to −70° C. and also no smectic phase other than SC* phase appeared. Further, its spontaneous polarization value was 8 nC/cm² at 25° C. and the tilt angle was 17°.

In addition, the mixture of the compound C and the compound D each in equal weights had the following phase transition points:

$$C \xrightarrow{6.0° C.} SC^* \xrightarrow{48.4° C.} SA \xrightarrow{58.3° C.} I$$

The above chiral smectic liquid crystal composition B was filled in a cell 2 μm thick provided with transparent electrodes each having PVA (polyvinyl alcohol) as an aligning agent applied thereonto and subjected to parallel aligning treatment by rubbing the surface, and when the resulting liquid crystal element was provided between two sheets of crossed polarizers, followed by impressing an electric field, change in the intensity of transmitted light was observed by impressing 15V. Response time was sought from the change in the intensity of transmitted light at that time to give about 150 μsec at 25° C.

As described above, it is seen that by blending the pyridine compound expressed by the formula (I) of the present invention with an optically active liquid crystal compound, a ferroelectric chiral smectic C liquid crystal composition having a broad temperature range of SC* phase and a superior response rate is obtained.

EXAMPLE 3 (COMPOSITION EXAMPLE 2)

The same liquid crystal component as used in Example 2 was used except that only its blending proportions were varied as follows to prepare a chiral smectic liquid crystal composition:

| | |
|---|---|
| liquid crystal composition A (mixture of compounds of the formula (I)) | 20% by weight |
| compound C | 20% by weight and |
| compound D | 60% by weight. |

With this liquid crystal composition, the temperature change of its texture was observed under a polarizing microscope so that it was found that the composition formed a ferroelectric chiral smectic C liquid crystal in the range of 11° to 61° C.; its spontaneous polarization value was 60 nC/cm² at 25° C. and its tilt angle was 26°. Further, when this liquid crystal composition was filled in a cell 2 μm thick as in Example 2, and the resulting liquid crystal element was provided between two sheets of crossed polarizers, and when an electric field was impressed, change in the intensity of transmitted light was observed by impressing 15V. Response time was sought from the change in the intensity of transmitted light at that time to give about 15 μsec at 25° C. In addition, a mixture of only compound C and compound D (1:3) had the following phase transition points:

$$C \xrightarrow{28.0°\ C.} SC^* \xrightarrow{72.3°\ C.} SA \xrightarrow{77.8°\ C.} Ch \xrightarrow{84.3°\ C.} I$$

What we claim is:

1. A halogen-containing pyridine compound expressed by the formula

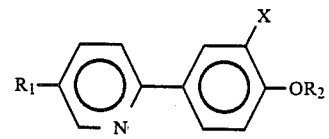

wherein X represents F or Cl, $R_1$ represents a straight chain alkyl group of 6 to 12 carbon atoms, and $R^2$ represents a straight claim alkyl group of 5 to 12 carbon atoms.

2. A compound according to claim 1 wherein said X represents F.

3. A chiral smectic C (SC*) liquid crystal composition comprising at least one compound expressed by the formula

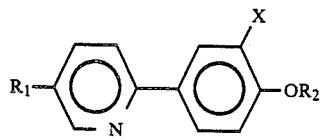

wherein X represents F or Cl and $R_1$ and $R_2$ each represent a straight chain alkyl group of 1 to 18 carbon atoms, and at least one optically active compound.

4. A chiral smectic C liquid crystal composition according to claim 3 wherein said optically active compound is a chiral smectic liquid crystal compound.

5. A light switching element which operates on the basis of ferroelectricity, said element containing a chiral smectic C liquid crystal composition comprising at least one compound expressed by the formula

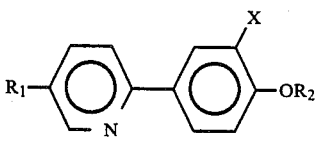

wherein X represents F or Cl and $R_1$ and $R_2$ each represent a straight chain alkyl group of 1 to 18 carbon atoms, and at least one optically active compound.

* * * * *